US012776401B2

(12) United States Patent
Malon

(10) Patent No.: US 12,776,401 B2
(45) Date of Patent: Oct. 27, 2026

(54) SUMMARIZING PREVALENT OPINIONS FOR MEDICAL DECISION-MAKING

(71) Applicant: NEC Laboratories America, Inc., Princeton, NJ (US)

(72) Inventor: Christopher Malon, Fort Lee, NJ (US)

(73) Assignee: NEC Corporation, Tokyo (JP)

( * ) Notice: Subject to any disclaimer, the term of this patent is extended or adjusted under 35 U.S.C. 154(b) by 178 days.

(21) Appl. No.: 18/439,274

(22) Filed: Feb. 12, 2024

(65) Prior Publication Data

US 2024/0274251 A1 Aug. 15, 2024

Related U.S. Application Data

(60) Provisional application No. 63/533,399, filed on Aug. 18, 2023, provisional application No. 63/532,340, filed on Aug. 11, 2023, provisional application No. 63/496,446, filed on Apr. 17, 2023, provisional application No. 63/484,534, filed on Feb. 13, 2023.

(51) Int. Cl.

| | |
|---|---|
| ***G16H 20/00*** | (2018.01) |
| ***G06F 40/205*** | (2020.01) |
| ***G06F 40/40*** | (2020.01) |

(52) U.S. Cl.

CPC ........... *G16H 20/00* (2018.01); *G06F 40/205* (2020.01); *G06F 40/40* (2020.01)

(58) Field of Classification Search

CPC ....... G16H 20/00; G06F 40/205; G06F 40/40; G06F 40/30

See application file for complete search history.

(56) References Cited

U.S. PATENT DOCUMENTS

| | | | | |
|---|---|---|---|---|
| 2002/0120187 | A1 * | 8/2002 | Eiffert | G16H 50/20 600/407 |
| 2006/0047538 | A1 * | 3/2006 | Condurso | G16H 40/67 705/3 |
| 2007/0078670 | A1 * | 4/2007 | Dave | G06F 40/253 705/347 |
| 2009/0265332 | A1 * | 10/2009 | Mushtaq | G06Q 30/0245 707/999.005 |
| 2014/0222834 | A1 * | 8/2014 | Parikh | G06F 16/345 707/748 |

(Continued)

OTHER PUBLICATIONS

Angelidis, S., Amplayo, R. K., Suhara, Y., Wang, X., & Lapata, M. (2021). Extractive opinion summarization in quantized transformer spaces. Transactions of the Association for Computational Linguistics, 9, 277-293. (Year: 2021).*

(Continued)

*Primary Examiner* — Philip H Lam

(74) *Attorney, Agent, or Firm* — Vincent Duffy

(57) ABSTRACT

Methods and systems for document summarization include splitting documents into sentences and sorting the sentences by a metric that promotes review opinion prevalence from the documents to generate a ranked list of sentences. Groups of sentences with similar embeddings are formed and a trained generalization encoder-decoder model is applied to output a common generalization of the sentences in each group. Sentences are added to a summary from the generalizations corresponding to the sentences in the ranked list, in rank-order, until a target summary length has been reached. An action is performed responsive to the summary.

20 Claims, 10 Drawing Sheets

(56) References Cited

U.S. PATENT DOCUMENTS

| | | | | |
|---|---|---|---|---|
| 2014/0351079 | A1* | 11/2014 | Dong | G06Q 30/0282 705/26.7 |
| 2019/0332666 | A1* | 10/2019 | Dadachev | G06F 40/284 |
| 2020/0059368 | A1* | 2/2020 | Stow | H04N 1/32283 |
| 2020/0168330 | A1* | 5/2020 | Schulman | G16H 10/60 |
| 2021/0303796 | A1* | 9/2021 | Elsahar | G06F 40/30 |
| 2022/0261668 | A1* | 8/2022 | Stumpe | G06N 3/094 |
| 2023/0164098 | A1* | 5/2023 | Cai | H04L 51/02 709/206 |
| 2023/0419042 | A1* | 12/2023 | Sabapathy | G06N 20/00 |

OTHER PUBLICATIONS

Raffel et al., "Exploring the Limits of Transfer Learning with a Unified Text-to-Text Transformer", Journal of Machine Learning Research 21 (2020) , Jun. 2020, pp. 1-67.

Kingma et al., "Adam: A Method for Stochastic Optimization", arXiv:1412.6980v9 [cs.LG] Jan. 30, 2017, pp. 1-15.

Holtzman et al., "The Curious Case of Neural Text DeGeneration", arXiv preprint arXiv:1904.09751, Apr. 22, 2019, pp. 1-16.

Clark et al., "Electra: Pre-Training Text Encoders as Discriminators Rather Than Generators", arXiv preprint arXiv:2003.10555, Mar. 23, 2020, pp. 1-18.

Liu et al., "RoBERTa: A Robustly Optimized BERT Pretraining Approach", arXiv:1907.11692v1 [cs.CL] Jul. 26, 2019, pp. 1-13.

Amplayo et al., "Unsupervised Opinion Summarization with Noising and Denoising", arXiv preprint arXiv:2004.10150. Apr. 21, 2020, pp. 1-12.

Manchego et al., "Asset: A Dataset for Tuning and Evaluation of Sentence Simplification Models with Multiple Rewriting Transformations", arXiv preprint arXiv:2005.00481, May 1, 2020, pp. 1-12.

Brazkinskas et al., "Unsupervised Opinion Summarization as Copycat-Review Generation", arXiv preprint arXiv:1911.02247, Nov. 6, 2019, pp. 1-19.

Lewis et al., "BART: Denoising Sequence-to-Sequence Pre-training for Natural Language Generation, Translation, and Comprehension", arXiv preprint arXiv:1910.13461, Oct. 29, 2019, pp. 1-10.

Ernst et al., "Summary-Source Proposition-level Alignment: Task, Datasets and Supervised Baseline", arXiv preprint arXiv:2009.00590, Sep. 1, 2020, pp. 1-13.

Iso et al., "Convex Aggregation for Opinion Summarization", Jan. 2021, pp. 264-269.

Fabbri et al., "QAFactEval: Improved QA-Based Factual Consistency Evaluation for Summarization", arXiv preprint arXiv:2112.08542, Dec. 16, 2021, pp. 1-15.

Laban et al., "SUMMAC: Re-Visiting NLI-based Models for Inconsistency Detection in Summarization", Transactions of the Association for Computational Linguistics, Feb. 9, 2022, pp. 1-15.

Chern et al., "Improving Factuality of Abstractive Summarization via Contrastive Reward Learning", arXiv preprint arXiv:2307.04507, Jul. 10, 2023, pp. 1-6.

Iso et al., "Noisy Pairing and Partial Supervision for Opinion Summarization", arXiv:2211.08723v1 [cs.CL] Nov. 16, 2022, pp. 1-11.

Bradley, "The Use of the Area Under the ROC Curve in the Evaluation of Machine Learning Algorithms", Pattern Recognition, 30(7), Jul. 1997, pp. 1145-1159.

Amplayo et al., "Beyond Opinion Mining: Summarizing Opinions of Customer Reviews", Jul. 2022, pp. 1-4.

Bowman et al., "A large annotated corpus for learning natural language inference", arXiv preprint arXiv:1508.05326. Aug. 21, 2015, pp. 632-642.

Conneau et al., "Supervised Learning of Universal Sentence Representations from Natural Language Inference Data", arXiv preprint arXiv:1705.02364, May 5, 2017, pp. 670-680.

Bowman et al., "Generating Sentences from a Continuous Space", arXiv preprint arXiv:1511.06349. Nov. 19, 2015, pp. 10-21.

Stanovsky et al., "Supervised Open Information Extraction", InProceedings of the 2018 Conference of the North American Chapter of the Association for Computational Linguistics: Human Language Technologies, vol. 1 (Long Papers) Jun. 2018, pp. 885-895.

Williams et al., "A Broad-Coverage Challenge Corpus for Sentence Understanding through Inference", arXiv preprint arXiv:1704.05426. Apr. 18, 2017, pp. 1112-1122.

See et al., "Get to The Point: Summarization with Pointer-Generator Networks", Proceedings of the 55th Annual Meeting of the Association for Computational Linguistics, Aug. 2017, pp. 1073-1083.

Angelidis et al., "Extractive Opinion Summarization in Quantized Transformer Spaces", Transactions of the Association for Computational Linguistics, Mar. 31, 2021, pp. 1-17.

Isonuma et al., "Unsupervised Abstractive Opinion Summarization by Generating Sentences with Tree-Structured Topic Guidance", Transactions of the Association for Computational Linguistics, Sep. 2021, pp. 945-961.

Lin, "Rouge: A Package for Automatic Evaluation of Summaries", In Text summarization branches out, Jul. 2004, pp. 74-81.

* cited by examiner

*Input*: Reviews $R = \{x_1, \ldots, x_m\}$
*Input*: Trivial statement $t$
*Input*: Target minimum length $N$
Collect all sentences $s_1, \ldots, s_n$ from $R$
foreach $j = 1, \ldots, n$
  if $C(t, s_j) = 0$
  then
    foreach $i = 1, \ldots, m$
      Compute $C(x_i, s_j)$
Let $i_1, \ldots, i_n$ be $\{1, \ldots, n\}$ sorted
  so that $Prev(R, \{s_{i_j}\}) \geq Prev(R, \{s_{i_{j+1}}\})$
Let $I \leftarrow \emptyset$
Let $j \leftarrow 0$
while $\sum_{i \in I} len(s_i) < N$ and $j < n$
  Let $j \leftarrow j + 1$
  if $C(t, x_{i_j}) = 0$ and $C(x_i, x_{i_j}) = 0$ for $i \in I$
  then Let $I \leftarrow I \cup \{i_j\}$
*Output*: Summary $\{s_i\}_{i \in I}$

FIG. 2

SUMMARIZING PREVALENT OPINIONS FOR MEDICAL DECISION-MAKING

RELATED APPLICATION INFORMATION

This application claims priority to U.S. Patent Application No. 63/484,534, filed on Feb. 13, 2023, to U.S. Patent Application No. 63/496,446, filed on Apr. 17, 2023, to U.S. Patent Application No. 63/532,340, filed on Aug. 11, 2023, and to U.S. Patent Application No. 63/533,399, filed on Aug. 18, 2023, each incorporated herein by reference in its entirety.

BACKGROUND

Technical Field

The present invention relates to natural language processing and, more particularly, to machine learning models for summarizing opinions.

Description of the Related Art

Opinion summarization is a natural language processing task that seeks to identify the most salient opinions expressed in a collection of documents. However, existing approaches to summarization do not distinguish between common opinions and those which are more rarely expressed.

SUMMARY

A method for document summarization includes splitting documents into sentences and sorting the sentences by a metric that promotes review opinion prevalence from the documents to generate a ranked list of sentences. Groups of sentences with similar embeddings are formed and a trained generalization encoder-decoder model is applied to output a common generalization of the sentences in each group. Sentences are added to a summary from the generalizations corresponding to the sentences in the ranked list, in rank-order, until a target summary length has been reached. An action is performed responsive to the summary.

A system for document generalization includes a hardware processor and a memory that stores a computer program. When executed by the hardware processor, the computer program causes the hardware processor to split documents into sentences, to sort the sentences by a metric that promotes review opinion prevalence from the documents to generate a ranked list of sentences, form groups of sentences with similar embeddings and to apply a trained generalization encoder-decoded model to output a common generalization of the sentences in each group, to add sentences to a summary from the generalizations corresponding to the sentences in the ranked list, in rank-order, until a target summary length has been reached, and to perform an action responsive to the summary.

These and other features and advantages will become apparent from the following detailed description of illustrative embodiments thereof, which is to be read in connection with the accompanying drawings.

BRIEF DESCRIPTION OF DRAWINGS

The disclosure will provide details in the following description of preferred embodiments with reference to the following figures wherein:

FIG. 2 is pseudo-code of an exemplary greedy summarization process, in accordance with an embodiment of the present invention;

DETAILED DESCRIPTION OF PREFERRED EMBODIMENTS

An automatic, reference-free metric for opinion prevalence may be used to guide summarization of opinions from a set of documents. This metric may give greater weight to opinions that are expressed more frequently in the documents. Additionally, opinions may be sorted according to how informative they are, based on measures of triviality and redundancy. A method for summarization is described that emphasizes common opinions. When used in conjunction with other metrics, such as fluency and coherence, a summarization may be generated which better captures the reliable informative opinions from a diverse collection.

Opinion summarization extracts salient opinions from a collection of reviews, such as for a product or service. However, large training sets of summaries are difficult to acquire, particularly those which provide a diverse set of reliable opinions for a variety of products. For large-scale data, providing human-generated references to guide the training may be impossible, because a human cannot practically remember all of the source text at once.

Figure 1:
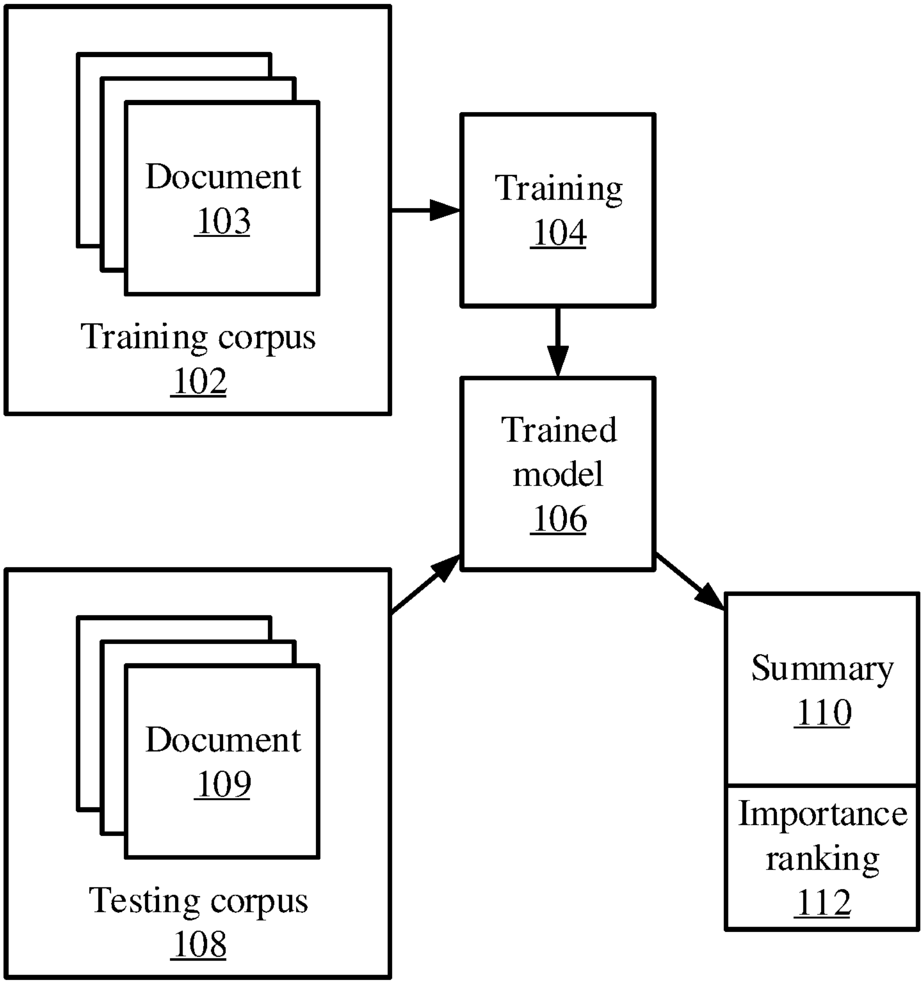
FIG. 1 is a block diagram of the training and use of a document summarization model, in accordance with an embodiment of the present invention.

Referring now to FIG. 1, a high-level view of the training and operation of an opinion summarization model is shown. A training corpus 102, made up of a set of training documents 103, is used in training 104 to generate a trained model 106. During operation, a testing corpus 108, made up of documents 109, is input to the trained model 106. The trained model 106 generates a summary 110 of the testing corpus. The summary 110 may be made up of a list of statements that reflect sentiments expressed in the testing corpus 108. An importance ranking 112 may further be generated that that ranks the statements in the summary 110 by their respective importance.

A variety of metrics can be used to determine the quality of a given summary. In fact, multiple such metrics may be used to determine an overall quality score. The present embodiments may use a metric that incorporates opinion prevalence, which weights how many times a given opinion appears within the testing corpus 108.

Given a binary classifier C(x,y), which returns 1 if a text x logically implies a text y and returns 0 otherwise, an opinion prevalence score may be defined for a summary S, having sentences $y_1, \ldots, y_n$ with respect to a set of reviews $R=\{x_1, \ldots, x_m\}$ for a given product or service p. Opinion prevalence should reward opinions that are expressed by multiple source reviews. For a given sentence y, this may be based on the quantity:

$$\frac{1}{|R|}\sum_{i=1}^{|R|} C(x_i, y)$$

For summaries with more than one sentence, there are two masks to apply to the classifier values. One mask may stop counting opinions that have already been mentioned to avoid redundancy. For $y_k$, this mask may be expressed as $\Pi_{j<k}(1-C(y_j,y_k))$.

A second mask may block conclusions that are so trivial that they follow from the fact that someone purchased the indicated product or service, without providing additional information about the person's experience. For example, a sentence t may be, "I bought p." If p is a sneaker, the obvious conclusions such as, "It is a shoe," or, "I wear it," could be logically expressed by every review without providing useful information. Therefore $C(x_i,y)$ may be masked with $1-C(t,y)$. In cases where the name of the product or service is not available, this mask may be omitted.

Attaching these masks to the formulation of the score, the definition of opinion prevalence may be expressed as:

$$Prev(R, S) = \frac{1}{mn}\sum_{k=1}^{n}\tau_k\rho_k\sum_{i=1}^{m}C(x_i y_k)$$

$$\tau_k = 1 - C(t, y_k)$$

$$\rho_k = \prod_{j<k}(1 - C(y_j, y_k))$$

The opinion prevalence may be compared among summaries of similar length. Otherwise, shorter summaries will have an advantage, if they can select the most prevalent opinions. Opinion prevalence provides scoring of the output of opinion summarization, without needing any reference summaries.

Referring now to FIG. 2, pseudo-code is shown for a summarization strategy that maximizes the opinion prevalence of an output summary. This method generates summaries with a high opinion prevalence, measured in the manner described above, and indeed may generate summaries with prevalence scores that are higher than summaries generated by human beings.

Most opinion summarization systems depend on splitting an input review into sentences and considering representations or properties of each sentence. In practice, input sentences may be long and complex, combining multiple different observations. This complexity can make it difficult to extract and relate the common assertions from different reviews. Text simplification may be used to pre-process the input sentences of source reviews.

Figure 3:
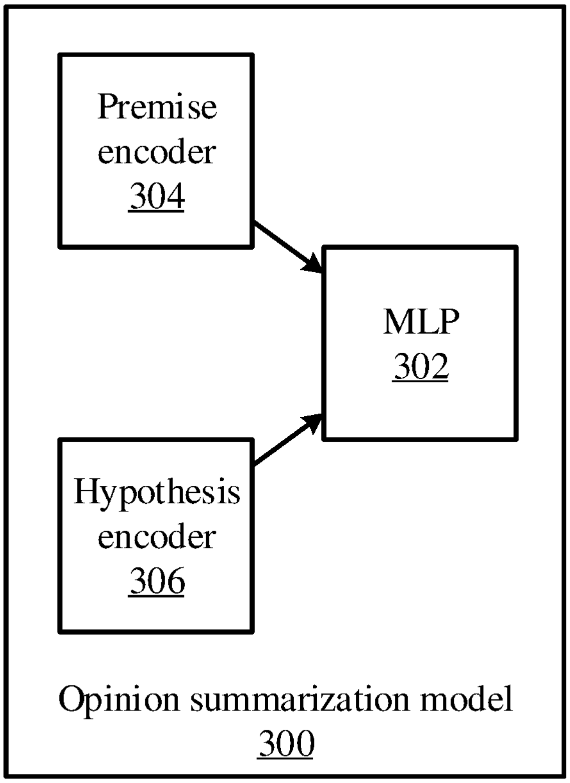
FIG. 3 is a block diagram of an exemplary opinion summarization model, in accordance with an embodiment of the present invention.

Referring now to FIG. 3, a diagram of an opinion comparison model 300 is shown. A multi-layer perceptron M 302 may be trained to solve natural language inference (NLI) tasks using comparison feature from encoders $E_P$ 304 (for the premise p) and $E_H$ 306 (for the hypothesis h). The encoders $E_P$ and $E_H$ may have the same weights. M may be trained for a binary classification task, with entailment or non-entailment. The term "entailment" may be understood as being equivalent to logical implication, determined in an NLI task. The comparison features may be expressed as the concatenation $(x;y;|x-y|;x*y)$, where $x=E_P(p)$, $y=E_H(h)$, and * is the element-wise product. M may be implemented as a two-layer perceptron with 128 hidden units and rectified linear unit (ReLU) non-linearities, outputting two logits. A transformer encoder model, such as an Electra base model may be used for the encoders. The encoders may be trained end-to-end together with M, on a mixture of NLI datasets that have been binarized, but not symmetrized.

For opinion summarization, groups of sentences that have a similar meaning may be collected from the reviews of a single product or service. The encoders $E(x)=E_P(x)=E_H(x)$ may be pre-computed for all sentences x in the product's reviews. The similarities cos(E(x),E(y)) may then be determined for all pairs of sentences (x,y) in the input reviews.

Although the number of comparisons grows quadratically with the number of sentences, the transformer network only needs to be run once for each sentence. Alternatively, the computation may be executed as $M(E(x);E(y);|E(x)-E(y)|;E(x)*E(y))$, which is not symmetric in x and y. M may be implemented as a small neural network, with a lower computational expense than the transformer E.

A ranking of the sentences may be introduced as a weighted count for each sentence of the number of other sentences that implies it or that are implied by it. The ranking may not set a hard similarity threshold for implication. Thus if the product reviews have sentences $x_1, \ldots, x_n$, then a ranking score $s_{ij}=e^{-\alpha(1-cos(E(x_i),E(x_j)))}$. At a first round, $$i_1 = \text{argmax}_i\left(\sum\nolimits_{j=1}^{n} s_{ij}\right)$$

is picked. At round m, then $$c_j = \max_{k<m} s_{i_k j}, \text{ and } i_m = \text{argmax}_{i \neq i_k \forall k<m}\left(\sum\nolimits_{j=1}^{n}(1-c_j)s_{ij}\right)$$

is picked. The rounds continue until the concatenation of the chosen sentences reaches a target length. The constant α may be selected based on a tradeoff between recall and precision for entailment at a score threshold. The ranking score gives high values to sentences that have a similar embedding to other sentences in the reviews, which were not similar to a previously selected sentence.

Although E is trained with M and not cos on non-symmetrized NLI instances, both cos and M have similar accuracies at their best thresholds on predicting the symmetrized relations between sentences. For example, a positive symmetrized relation is found if either x implies y or y implies x.

The sentences $x_{i_1}, \ldots, x_{i_m}$ may be used as a summary. Because of the accumulation of similarity factors, the chosen sentences will be highly implied. Because of the discount of $(1-c_j)$ of contributions to previously chosen sentences, the summary sentences should be non-redundant. This gives an extractive summarization of the input. This approach generates summaries with prevalence scores near human-level performance.

Instead of taking the extractive summary from the embeddings, for each k=1, . . . , m, the group $G_{i_k}$ of statements $x_1$ may be considered, such that $s_{i_k i}>0.1$. The text of each statement in a single group may be concatenated with a vertical var separator and provided as input to a sequence-to-sequence model that is trained to output a generalization of the group's statements.

The training data for this sequence-to-sequence model is established by first running an NLI model on each pair of review sentences for the same product, for example taking up to eight reviews. The training set may be partitioned into a training subset (e.g., 80%), a development subset (e.g., 10%), and a testing subset (e.g., 10%). Weakly entailed decisions may be understood as those which generate a probability below a first threshold, while strongly entailed decisions may be understood as those which generate a probability above a second threshold.

Given these entailment decisions, the sentences may be sorted by the number of other sentences that strongly entail them. Sentences may be selected in order that are not weakly entailed by previously selected sentences, as long as each is strongly entailed by at least one other sentence.

Each selected example becomes the target sequence in an example, where the source sequence is the set of sentences which strongly entail it, concatenated with a vertical bar separator. A model may be trained using a cross-entropy loss to predict target sequences from source sequences.

Figure 4:
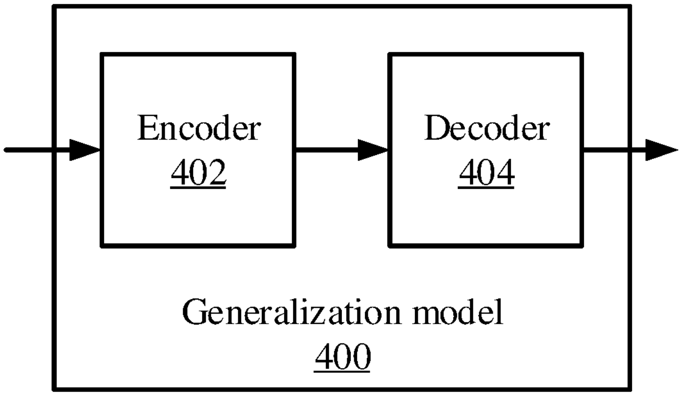
FIG. 4 is a block diagram of an exemplary opinion generalization model, in accordance with an embodiment of the present invention.

Referring now to FIG. 4, a generalization model 400 is shown. The trained generalization model 400 may be applied to the groups $G_{i_k}$ in the test set obtained from the embedder. Each group represents sentences with a common, similar meaning.

Concatenating the model's outputs on each group gives summaries with average opinion prevalence scores that are superior to human summaries. The generalization model 400 may be implemented with an encoder 402 and a decoder 404. The encoder 402 accepts one or more input statements, for example sentences representing opinions, and outputs vector representations of the input statements in a latent space. The decoder 404 then accepts the vector representations and generates output statements that are entailed by the input statements. In some embodiments, multiple input statements may be provided to generate a single output statement which is logically implied by the multiple input statements.

The informativeness of a summary S, having sentences $y_1, \ldots, y_n$, may be defined with respect to a set of m reviews $R=\{x_1, \ldots, x_m\}$ of a product p, in contrast to a set of m' reviews $$R' = \{x'_1, \ldots, x'_{m'}\}$$

of other products p'≠p in the same category as p, as:

$$\frac{1}{n}\sum_{k=1}^{n}\tau_k\rho_k\frac{(1+m')\left(1+\sum_{i=1}^{m}C(x_i, y_k)\right)}{(1+m)\left(1+\sum_{i=1}^{m'}C(x'_i, y_k)\right)}$$

where $\tau_k$ and $\rho_k$ are the triviality and redundancy masks. The generalization model may be modified to output more informative statements by contrastive learning, sorting the sentences y in a group according to informativeness, as single-sentence summaries S={y} rather than by the number of strong entailments. A ranking of model outputs by their informativeness may be used to further fine-tune the generalization model by contrastive learning.

Figure 5:
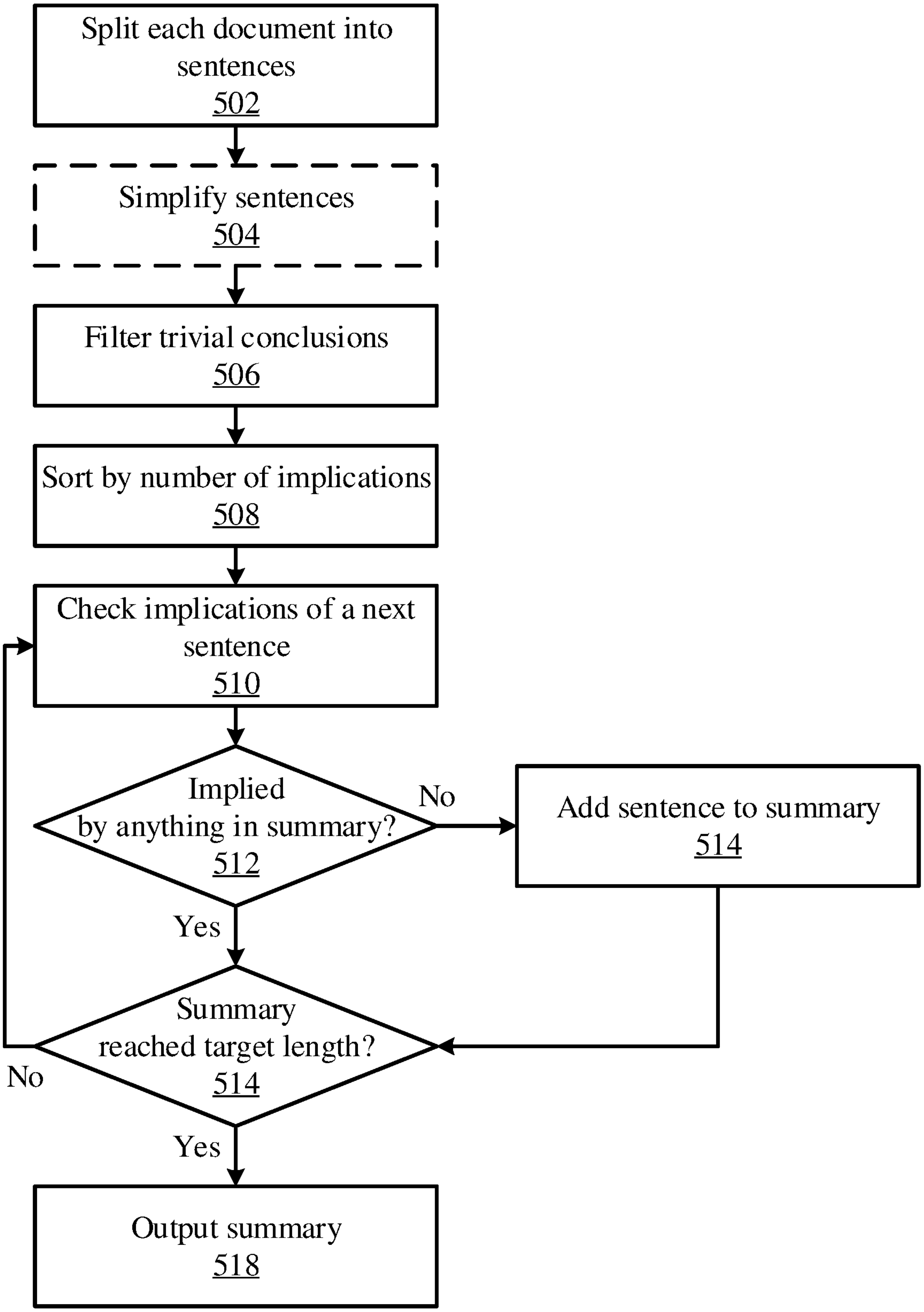
FIG. 5 is a block/flow diagram of a method for opinion summarization, in accordance with an embodiment of the present invention.

Referring now to FIG. 5, a method for summarizing the opinions of a set of reviews is shown. Block 502 splits each document into sentences, where each document corresponds to a respective review for a particular product or service. The sentences may optionally be simplified by block 504, as described above, to separate complex sentiments into simpler expressions. Block 506 filters trivial conclusions, such as those which would logically follow from the fact that someone purchased the product or service in question.

Block 508 sorts the sentences according to a number of implications, counting the number of other documents which imply each document according to an NLI model. Block 510 then selects a highest ranked remaining sentence from the sorted sentences. Starting with an empty summary, block 512 determines whether the selected sentence is implied by anything already in the summary. If not, block 514 adds the sentence to the summary. Block 514 determines whether the summary has reached a target length. If not, processing returns to block 510 and a next most-implied sentence is selected. If so, processing ends and the sentences added to the summary are output by block 518.

Figure 6:
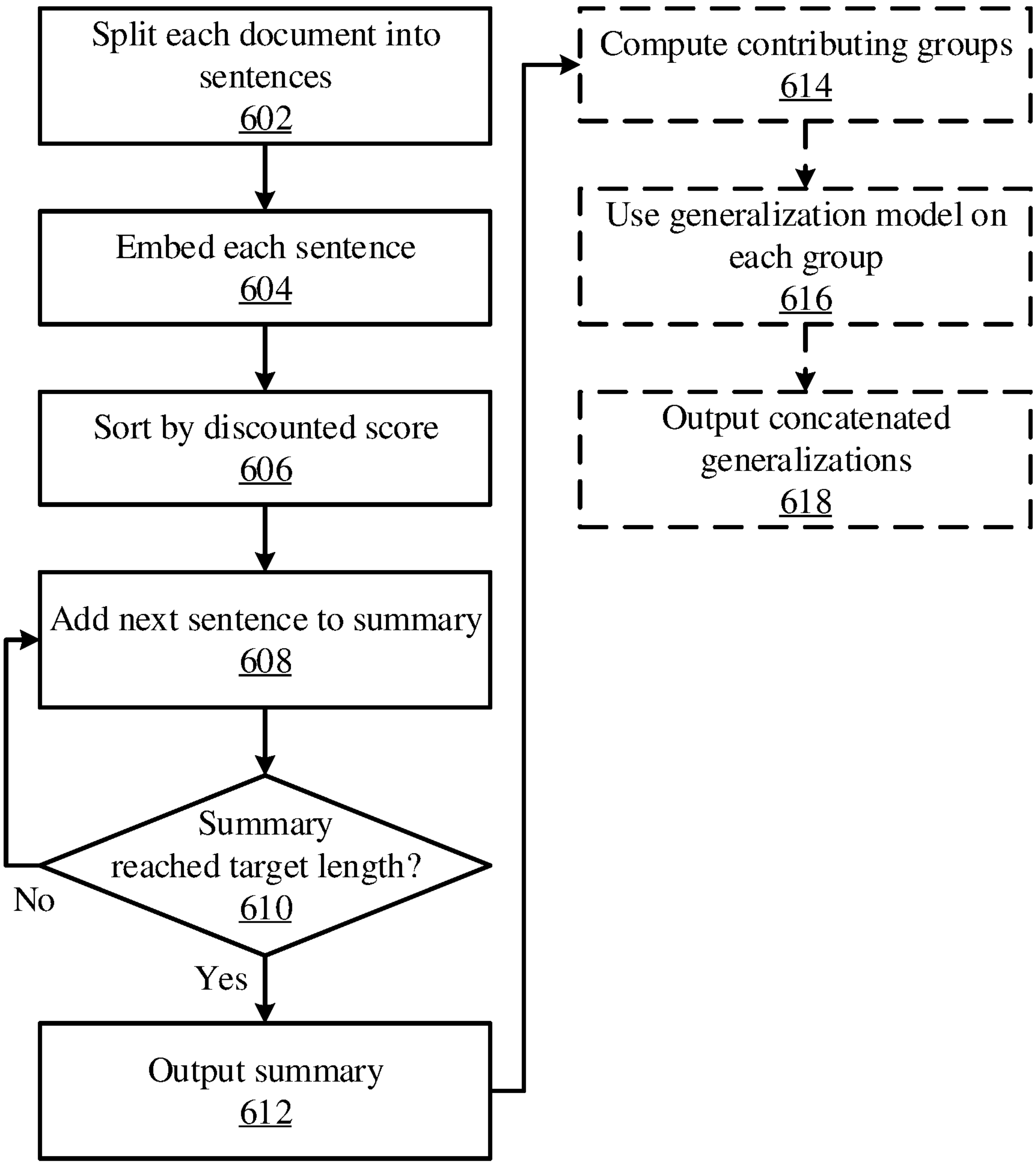
FIG. 6 is a block/flow diagram of a method for opinion summarization, in accordance with an embodiment of the present invention.

Referring now to FIG. 6, a method of generating summaries by embedding is shown. Block 602 splits the review documents into sentences as described above. Block 604 embeds each sentence using the encoder E, rendering the sentences as respective vector representations. Block 606 calculates a discounted score for each sentence as described above and sorts the sentences accordingly. Block 608 then adds a highest-scoring sentence to the summary and block 610 checks whether the summary has reached its target length. If not, a next-highest scoring sentence is added to the summary in block 608. This process repeats until the target length is reached, at which point block 612 outputs the selected sentences as the summary.

Further generalization may optionally be performed on the summary. Block 614 determines the groups (e.g., $G_{i_k}$) contributing to each sentence. Block 616 uses a generalization model on each of the groups, and block 618 outputs concatenated generalizations from each group as the summary.

Figure 7:
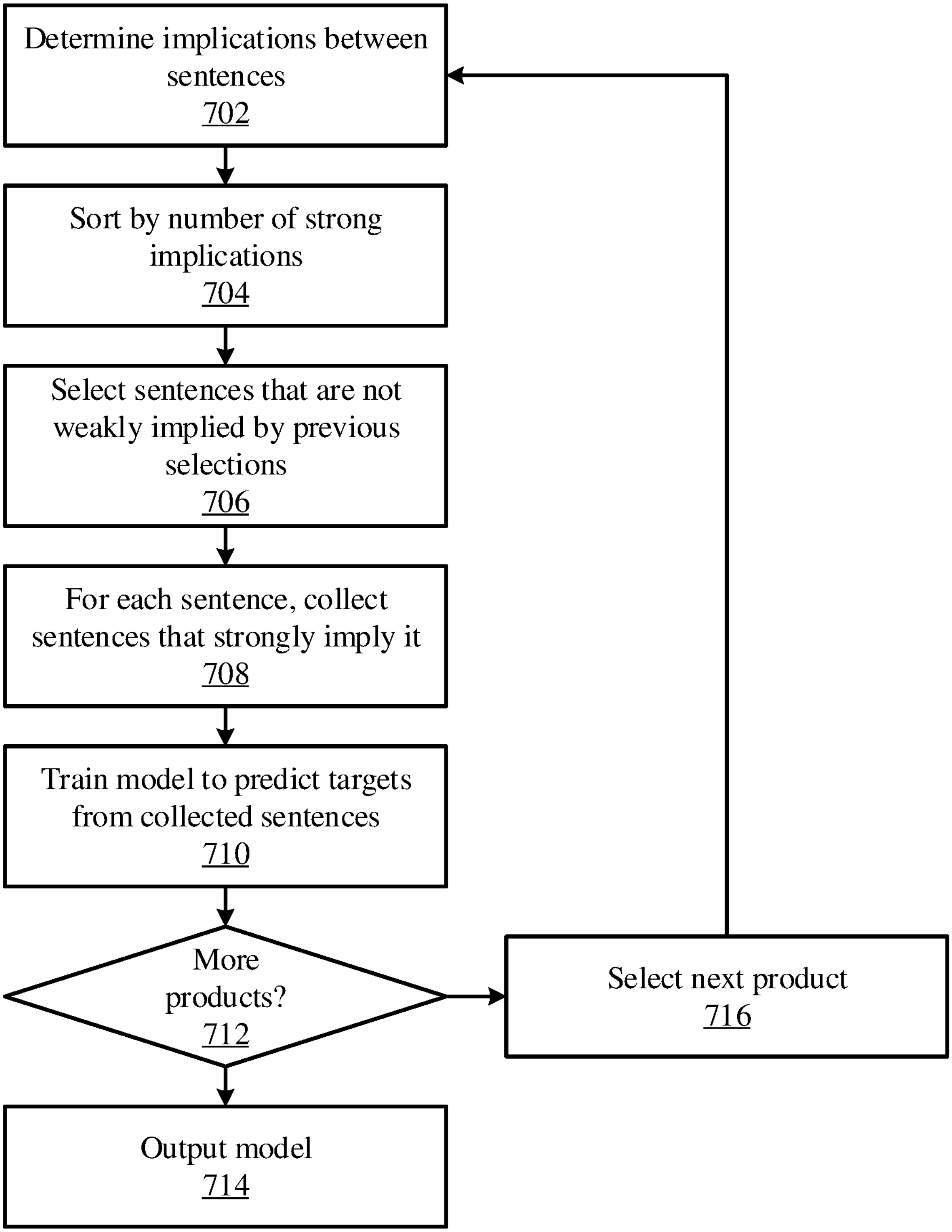
FIG. 7 is a block/flow diagram of a method of training an opinion summarization model, in accordance with an embodiment of the present invention.

Referring now to FIG. 7, a method for training a generalization model is shown. A set of reviews is used as training data, which may pertain to multiple products or services. For a first product or service, block 702 determines implications between pairs of sentences of the reviews using a trained NLI model. Block 704 sorts the sentences by the number of strong implications (e.g., with a probability output by the NLI model that is above a strong-implication threshold). Block 706 then selects sentences that are not weakly implied by previous selections (e.g., with a probability output by the NLI model that is below a weak-implication threshold).

For each selected sentence, block 708 collects the sentences that strongly imply it as a source sequence. Block 710 then trains the generalization model to predict targets from source sequences with a cross-entropy loss.

Block 712 determines whether there are additional products or services to use for training. If so, block 716 selects a next product or service and block 702 determines the implications between sentences in reviews related to the next product. If all of the products/services have been used for training, then block 714 outputs the trained generalization model.

Figure 8:
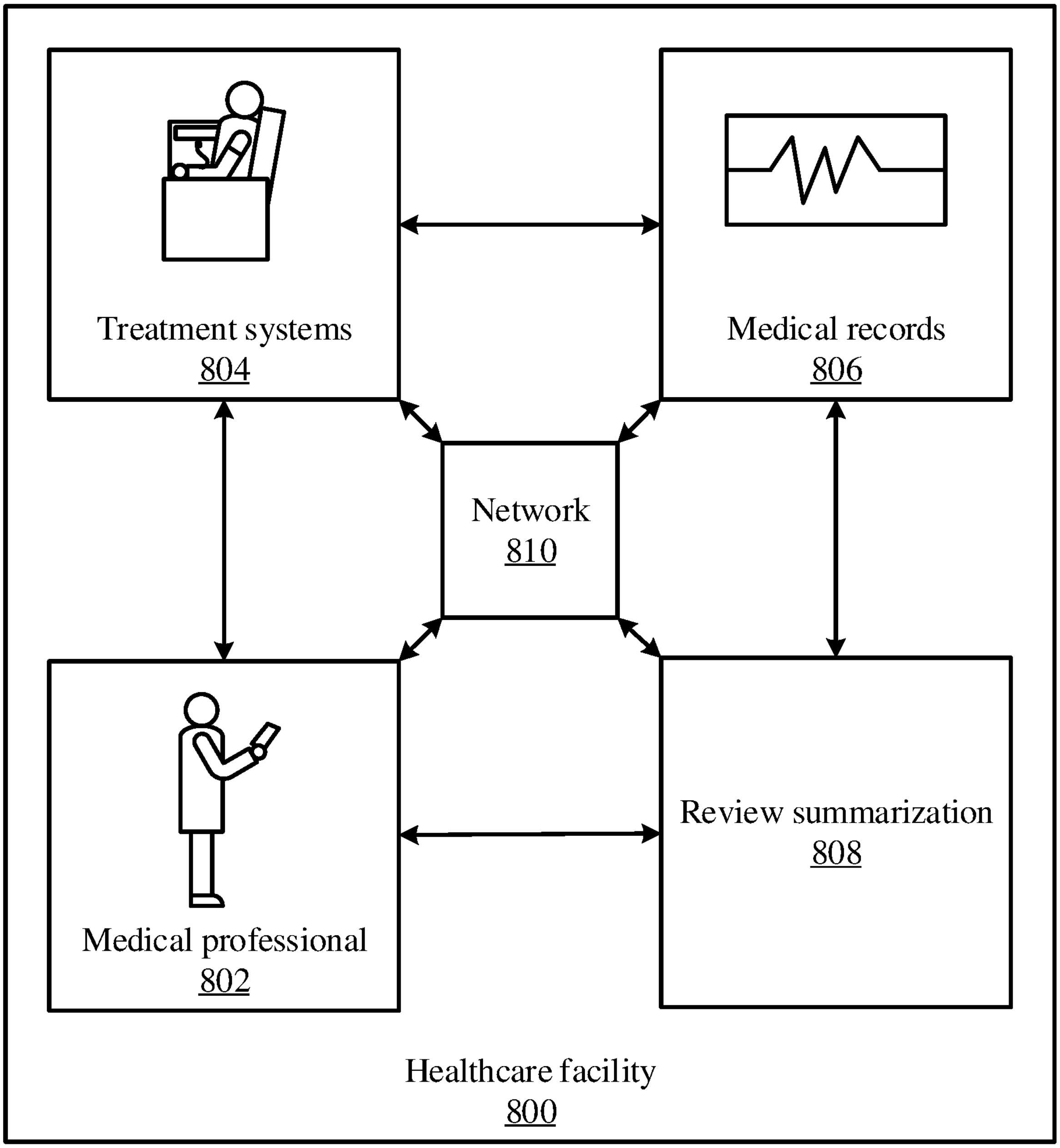
FIG. 8 is a block diagram showing review summarization in the context of a healthcare facility, in accordance with an embodiment of the present invention.

Referring now to FIG. 8, a diagram of review summarization is shown in the context of a healthcare facility 800. Review summarization 808 may be used to guide decision-making for medical professionals 802, for example in determining which healthcare products are appropriate to treat a given patient or to use in the healthcare facility 800. Automated review summarization can make it easier for the medical professionals 802 to understand the costs and benefits of a given product in the context of the patient's medical status.

The healthcare facility may include one or more medical professionals 802 who review information from a patient's medical records 806 to determine their healthcare and treatment needs. Treatment systems 804 may furthermore monitor patient status to generate medical records 806 and may be designed to automatically administer and adjust treatments as needed. In a specific example, the reviews may pertain to supplements or medications that may be provided to a user, such as vitamins and nutritional supplements. In another example, the reviews may pertain to mobility aids, such as canes, walkers, wheelchairs, etc., or to prostheses.

Based on information drawn from a body of reviews for one or more relevant products, review summarization 808 may identify a set of important and prevalent opinions about the products. The medical professionals 802 may then make decisions about patient healthcare based on the review summary, for example determining which product is most effective for a patient's particular needs.

The different elements of the healthcare facility 800 may communicate with one another via a network 810, for example using any appropriate wired or wireless communications protocol and medium. Thus review summarization 808 send reports to medical professionals 802, who may make healthcare decisions in the context of the patient's medical records 806. In some cases, the review summarization 808 may be integrated with an automated treatment system 804, which may automatically trigger treatment changes for a patient in response to information gleaned from a review summary. For example, if a review summary indicates that a given product is dangerous, then the treatment system 804 may automatically cease treatment with that product until a medical professional 802 can review it.

Figure 9:
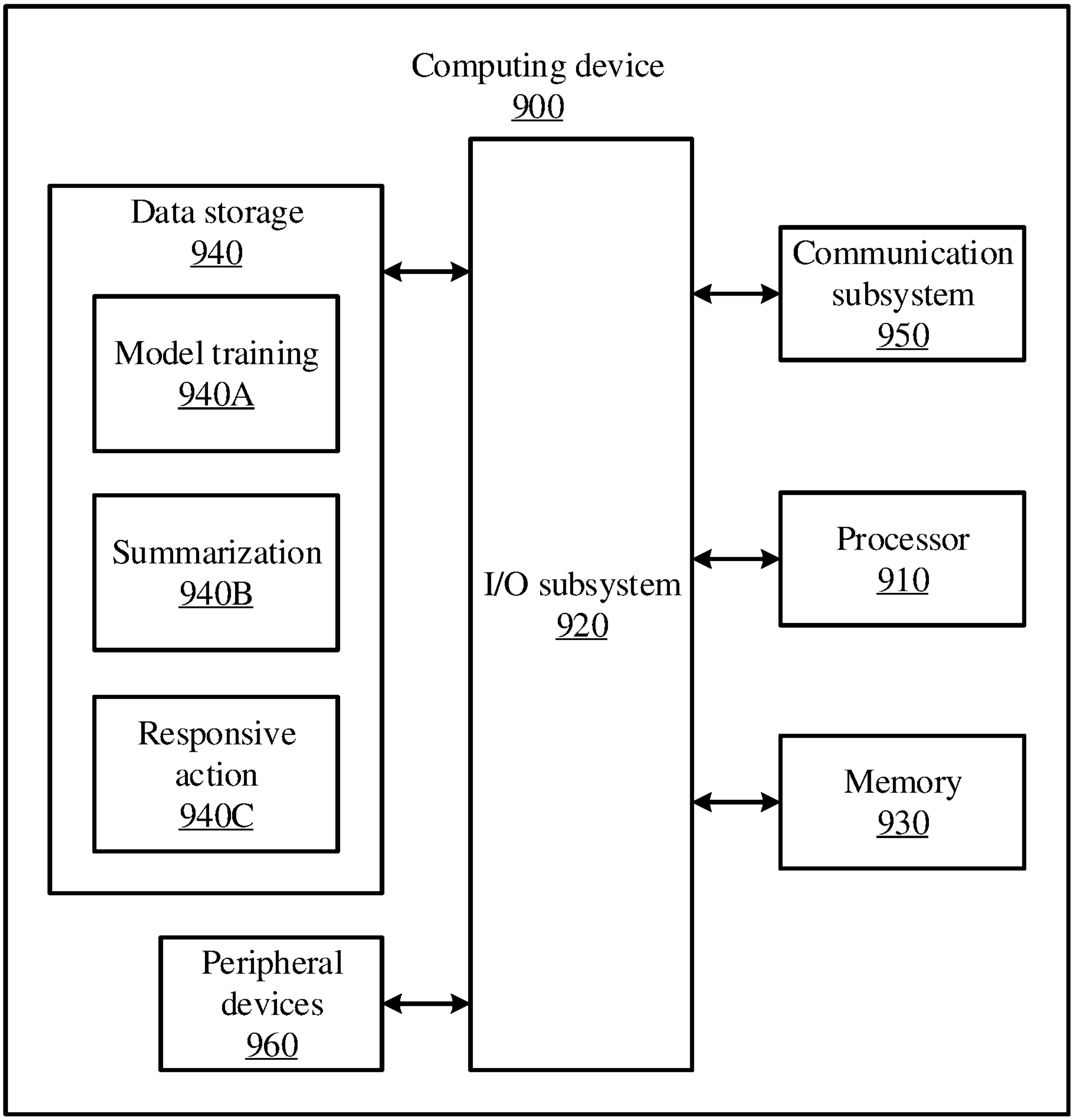
FIG. 9 is a block diagram of a computing device that can perform review summarization, in accordance with an embodiment of the present invention.

Referring now to FIG. 9, an exemplary computing device 900 is shown, in accordance with an embodiment of the present invention. The computing device 900 is configured to perform review summarization.

The computing device 900 may be embodied as any type of computation or computer device capable of performing the functions described herein, including, without limitation, a computer, a server, a rack based server, a blade server, a workstation, a desktop computer, a laptop computer, a notebook computer, a tablet computer, a mobile computing device, a wearable computing device, a network appliance, a web appliance, a distributed computing system, a processor-based system, and/or a consumer electronic device. Additionally or alternatively, the computing device 900 may be embodied as one or more compute sleds, memory sleds, or other racks, sleds, computing chassis, or other components of a physically disaggregated computing device.

As shown in FIG. 9, the computing device 900 illustratively includes the processor 910, an input/output subsystem 920, a memory 930, a data storage device 940, and a communication subsystem 950, and/or other components and devices commonly found in a server or similar computing device. The computing device 900 may include other or additional components, such as those commonly found in a server computer (e.g., various input/output devices), in other embodiments. Additionally, in some embodiments, one or more of the illustrative components may be incorporated in, or otherwise form a portion of, another component. For example, the memory 930, or portions thereof, may be incorporated in the processor 910 in some embodiments.

The processor 910 may be embodied as any type of processor capable of performing the functions described herein. The processor 910 may be embodied as a single processor, multiple processors, a Central Processing Unit(s) (CPU(s)), a Graphics Processing Unit(s) (GPU(s)), a single or multi-core processor(s), a digital signal processor(s), a microcontroller(s), or other processor(s) or processing/controlling circuit(s).

The memory 930 may be embodied as any type of volatile or non-volatile memory or data storage capable of performing the functions described herein. In operation, the memory 930 may store various data and software used during operation of the computing device 900, such as operating systems, applications, programs, libraries, and drivers. The memory 930 is communicatively coupled to the processor 910 via the I/O subsystem 920, which may be embodied as circuitry and/or components to facilitate input/output operations with the processor 910, the memory 930, and other components of the computing device 900. For example, the I/O subsystem 920 may be embodied as, or otherwise include, memory controller hubs, input/output control hubs, platform controller hubs, integrated control circuitry, firmware devices, communication links (e.g., point-to-point links, bus links, wires, cables, light guides, printed circuit board traces, etc.), and/or other components and subsystems to facilitate the input/output operations. In some embodiments, the I/O subsystem 920 may form a portion of a system-on-a-chip (SOC) and be incorporated, along with the processor 910, the memory 930, and other components of the computing device 900, on a single integrated circuit chip.

The data storage device 940 may be embodied as any type of device or devices configured for short-term or long-term storage of data such as, for example, memory devices and circuits, memory cards, hard disk drives, solid state drives, or other data storage devices. The data storage device 940 can store program code 940A for training a model, 940B for performing review summarization, and/or 940C for performing an automatic action responsive to a review summary. Any or all of these program code blocks may be included in a given computing system. The communication subsystem 950 of the computing device 900 may be embodied as any network interface controller or other communication circuit, device, or collection thereof, capable of enabling communications between the computing device 900 and other remote devices over a network. The communication subsystem 950 may be configured to use any one or more communication technology (e.g., wired or wireless communications) and associated protocols (e.g., Ethernet, InfiniBand®, Bluetooth®, Wi-Fi®, WiMAX, etc.) to effect such communication.

As shown, the computing device 900 may also include one or more peripheral devices 960. The peripheral devices 960 may include any number of additional input/output devices, interface devices, and/or other peripheral devices. For example, in some embodiments, the peripheral devices 960 may include a display, touch screen, graphics circuitry, keyboard, mouse, speaker system, microphone, network interface, and/or other input/output devices, interface devices, and/or peripheral devices.

Of course, the computing device 900 may also include other elements (not shown), as readily contemplated by one of skill in the art, as well as omit certain elements. For example, various other sensors, input devices, and/or output devices can be included in computing device 900, depending upon the particular implementation of the same, as readily understood by one of ordinary skill in the art. For example, various types of wireless and/or wired input and/or output devices can be used. Moreover, additional processors, controllers, memories, and so forth, in various configurations can also be utilized. These and other variations of the processing system 900 are readily contemplated by one of ordinary skill in the art given the teachings of the present invention provided herein.

Figure 10:
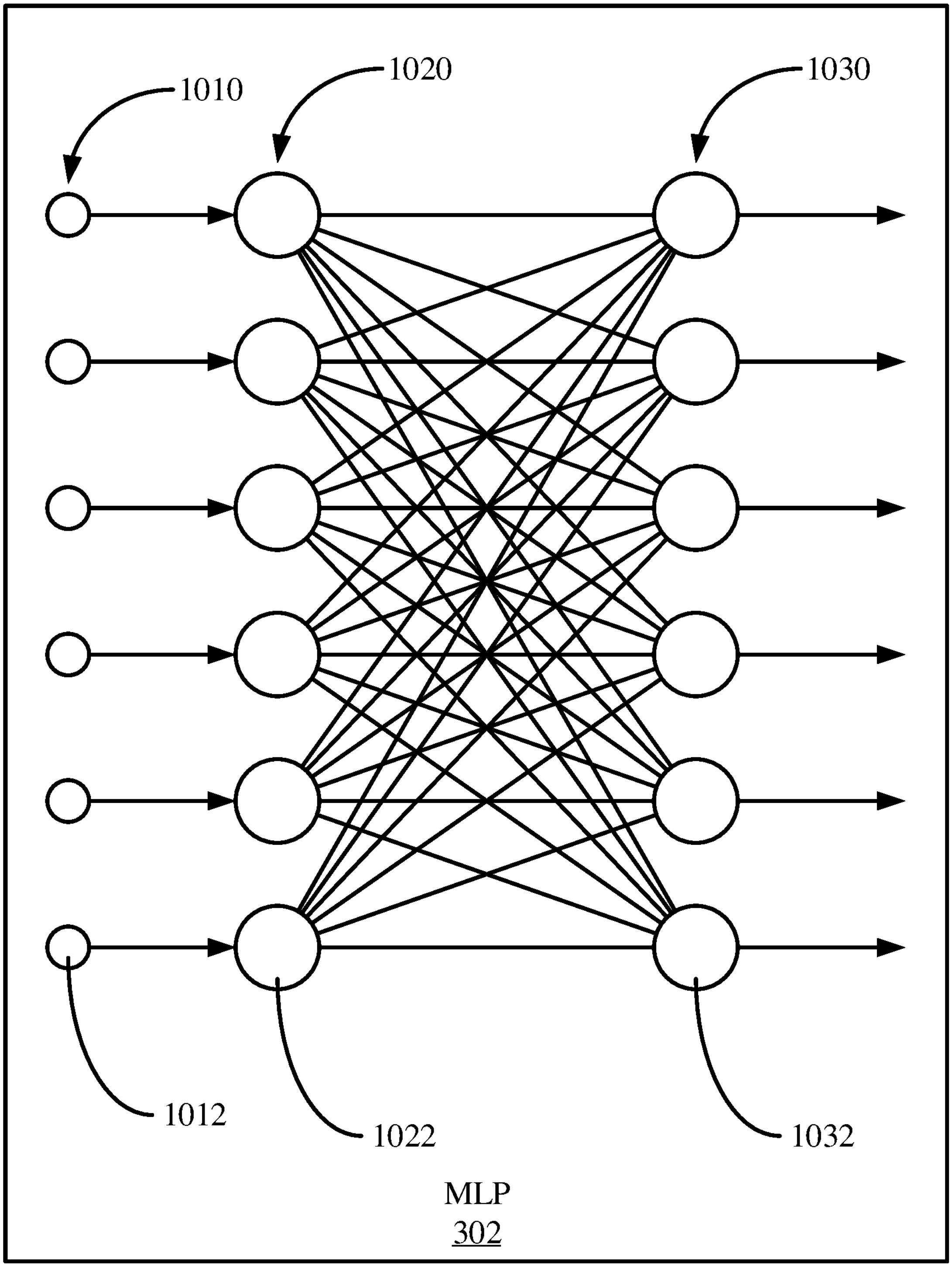
FIG. 10 is a diagram of an exemplary neural network architecture that can be used to implement part of the generalization model, in accordance with an embodiment of the present invention.
Figure 11:
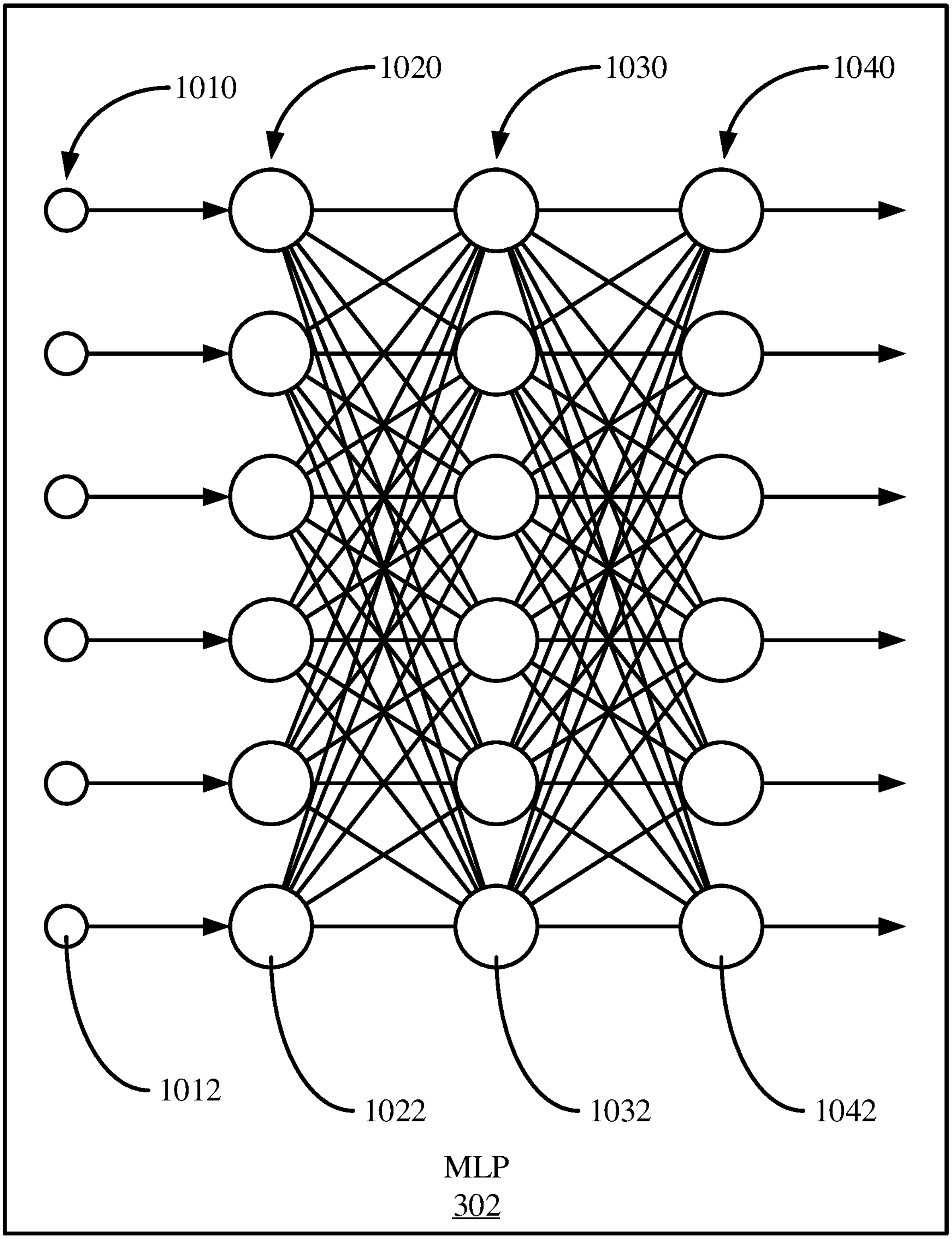
FIG. 11 is a diagram of an exemplary neural network architecture that can be used to implement part of the generalization model, in accordance with an embodiment of the present invention.

Referring now to FIGS. 10 and 11, exemplary neural network architectures are shown, which may be used to implement parts of the present models, such as the MLP 302. A neural network is a generalized system that improves its functioning and accuracy through exposure to additional empirical data. The neural network becomes trained by exposure to the empirical data. During training, the neural network stores and adjusts a plurality of weights that are applied to the incoming empirical data. By applying the adjusted weights to the data, the data can be identified as belonging to a particular predefined class from a set of classes or a probability that the input data belongs to each of the classes can be output.

The empirical data, also known as training data, from a set of examples can be formatted as a string of values and fed into the input of the neural network. Each example may be associated with a known result or output. Each example can be represented as a pair, (x,y), where x represents the input data and y represents the known output. The input data may include a variety of different data types, and may include multiple distinct values. The network can have one input node for each value making up the example's input data, and a separate weight can be applied to each input value. The input data can, for example, be formatted as a vector, an array, or a string depending on the architecture of the neural network being constructed and trained.

The neural network "learns" by comparing the neural network output generated from the input data to the known values of the examples, and adjusting the stored weights to minimize the differences between the output values and the known values. The adjustments may be made to the stored weights through back propagation, where the effect of the weights on the output values may be determined by calculating the mathematical gradient and adjusting the weights in a manner that shifts the output towards a minimum difference. This optimization, referred to as a gradient descent approach, is a non-limiting example of how training may be performed. A subset of examples with known values that were not used for training can be used to test and validate the accuracy of the neural network.

During operation, the trained neural network can be used on new data that was not previously used in training or validation through generalization. The adjusted weights of the neural network can be applied to the new data, where the weights estimate a function developed from the training examples. The parameters of the estimated function which are captured by the weights are based on statistical inference.

In layered neural networks, nodes are arranged in the form of layers. An exemplary simple neural network has an input layer 1020 of source nodes 1022, and a single computation layer 1030 having one or more computation nodes 1032 that also act as output nodes, where there is a single computation node 1032 for each possible category into which the input example could be classified. An input layer 1020 can have a number of source nodes 1022 equal to the number of data values 1012 in the input data 1010. The data values 1012 in the input data 1010 can be represented as a column vector. Each computation node 1032 in the computation layer 1030 generates a linear combination of weighted values from the input data 1010 fed into input nodes 1020, and applies a non-linear activation function that is differentiable to the sum. The exemplary simple neural network can perform classification on linearly separable examples (e.g., patterns).

A deep neural network, such as a multilayer perceptron, can have an input layer 1020 of source nodes 1022, one or more computation layer(s) 1030 having one or more computation nodes 1032, and an output layer 1040, where there is a single output node 1042 for each possible category into which the input example could be classified. An input layer 1020 can have a number of source nodes 1022 equal to the number of data values 1012 in the input data 1010. The computation nodes 1032 in the computation layer(s) 1030 can also be referred to as hidden layers, because they are between the source nodes 1022 and output node(s) 1042 and are not directly observed. Each node 1032, 1042 in a computation layer generates a linear combination of weighted values from the values output from the nodes in a previous layer, and applies a non-linear activation function that is differentiable over the range of the linear combination. The weights applied to the value from each previous node can be denoted, for example, by $w_1, w_2, \ldots w_{n-1}, w_n$. The output layer provides the overall response of the network to the input data. A deep neural network can be fully connected, where each node in a computational layer is connected to all other nodes in the previous layer, or may have other configurations of connections between layers. If links between nodes are missing, the network is referred to as partially connected.

Training a deep neural network can involve two phases, a forward phase where the weights of each node are fixed and the input propagates through the network, and a backwards phase where an error value is propagated backwards through the network and weight values are updated.

The computation nodes 1032 in the one or more computation (hidden) layer(s) 1030 perform a nonlinear transformation on the input data 1012 that generates a feature space. The classes or categories may be more easily separated in the feature space than in the original data space.

Embodiments described herein may be entirely hardware, entirely software or including both hardware and software elements. In a preferred embodiment, the present invention is implemented in software, which includes but is not limited to firmware, resident software, microcode, etc.

Embodiments may include a computer program product accessible from a computer-usable or computer-readable medium providing program code for use by or in connection with a computer or any instruction execution system. A computer-usable or computer readable medium may include any apparatus that stores, communicates, propagates, or transports the program for use by or in connection with the instruction execution system, apparatus, or device. The medium can be magnetic, optical, electronic, electromagnetic, infrared, or semiconductor system (or apparatus or device) or a propagation medium. The medium may include a computer-readable storage medium such as a semiconductor or solid state memory, magnetic tape, a removable computer diskette, a random access memory (RAM), a read-only memory (ROM), a rigid magnetic disk and an optical disk, etc.

Each computer program may be tangibly stored in a machine-readable storage media or device (e.g., program memory or magnetic disk) readable by a general or special purpose programmable computer, for configuring and controlling operation of a computer when the storage media or device is read by the computer to perform the procedures described herein. The inventive system may also be considered to be embodied in a computer-readable storage medium, configured with a computer program, where the storage medium so configured causes a computer to operate in a specific and predefined manner to perform the functions described herein.

A data processing system suitable for storing and/or executing program code may include at least one processor coupled directly or indirectly to memory elements through a system bus. The memory elements can include local memory employed during actual execution of the program code, bulk storage, and cache memories which provide temporary storage of at least some program code to reduce the number of times code is retrieved from bulk storage during execution. Input/output or I/O devices (including but not limited to keyboards, displays, pointing devices, etc.) may be coupled to the system either directly or through intervening I/O controllers.

Network adapters may also be coupled to the system to enable the data processing system to become coupled to other data processing systems or remote printers or storage devices through intervening private or public networks. Modems, cable modem and Ethernet cards are just a few of the currently available types of network adapters.

As employed herein, the term "hardware processor subsystem" or "hardware processor" can refer to a processor, memory, software or combinations thereof that cooperate to perform one or more specific tasks. In useful embodiments, the hardware processor subsystem can include one or more data processing elements (e.g., logic circuits, processing circuits, instruction execution devices, etc.). The one or more data processing elements can be included in a central processing unit, a graphics processing unit, and/or a separate processor- or computing element-based controller (e.g., logic gates, etc.). The hardware processor subsystem can include one or more on-board memories (e.g., caches, dedicated memory arrays, read only memory, etc.). In some embodiments, the hardware processor subsystem can include one or more memories that can be on or off board or that can be dedicated for use by the hardware processor subsystem (e.g., ROM, RAM, basic input/output system (BIOS), etc.).

In some embodiments, the hardware processor subsystem can include and execute one or more software elements. The one or more software elements can include an operating system and/or one or more applications and/or specific code to achieve a specified result.

In other embodiments, the hardware processor subsystem can include dedicated, specialized circuitry that performs one or more electronic processing functions to achieve a specified result. Such circuitry can include one or more application-specific integrated circuits (ASICs), field-programmable gate arrays (FPGAs), and/or programmable logic arrays (PLAs).

These and other variations of a hardware processor subsystem are also contemplated in accordance with embodiments of the present invention.

Reference in the specification to "one embodiment" or "an embodiment" of the present invention, as well as other variations thereof, means that a particular feature, structure, characteristic, and so forth described in connection with the embodiment is included in at least one embodiment of the present invention. Thus, the appearances of the phrase "in one embodiment" or "in an embodiment", as well any other variations, appearing in various places throughout the specification are not necessarily all referring to the same embodiment. However, it is to be appreciated that features of one or more embodiments can be combined given the teachings of the present invention provided herein.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended for as many items listed.

The foregoing is to be understood as being in every respect illustrative and exemplary, but not restrictive, and the scope of the invention disclosed herein is not to be determined from the Detailed Description, but rather from the claims as interpreted according to the full breadth permitted by the patent laws. It is to be understood that the embodiments shown and described herein are only illustrative of the present invention and that those skilled in the art may implement various modifications without departing from the scope and spirit of the invention. Those skilled in the art could implement various other feature combinations without departing from the scope and spirit of the invention. Having thus described aspects of the invention, with the details and particularity required by the patent laws, what is claimed and desired protected by Letters Patent is set forth in the appended claims.

What is claimed is:

1. A computer-implemented method for document summarization, comprising:

splitting documents into sentences;

sorting the sentences by a metric that promotes review opinion prevalence from the documents to generate a ranked list of sentences, with prevalence being expressed as $$Prev(R, S) = \frac{1}{mn}\sum_{k=1}^{n}\tau_k\rho_k\sum_{i=1}^{m}C(x_i y_k)$$

where R is a set of reviews, S is a summary, n is a number of sentences, m is a number of reviews, k is an index, i is an index, $\tau_k\rho_k$ is a mask, and $C(\cdot,\cdot)$ is a classifier function for texts x and y;

forming groups of sentences with similar embeddings and applying a trained generalization encoder-decoder model to output a common generalization of the sentences in each group;

adding sentences to a summary from the common generalizations corresponding to the sentences in the ranked list, in rank-order, until a target summary length has been reached; and performing an action responsive to the summary.

2. The method of claim 1, further comprising simplifying the sentences before sorting.

3. The method of claim 1, further comprising filtering trivial conclusions from the sentences before sorting.

4. The method of claim 1, wherein sorting the sentences includes sorting by a number of implications each sentence has from other sentences.

5. The method of claim 1, wherein sorting the sentences includes assigning a score to each sentence based on a cosine comparison of encoded sentence representations.

6. The method of claim 5, wherein the score is further discounted by a maximum of previous scores for each sentence.

7. The method of claim 1, wherein the documents are reviews for a healthcare product and wherein performing the action includes altering a treatment for a patient based on the summary.

8. The method of claim 7, wherein altering the treatment for the patient includes automatically ceasing a treatment that is indicated as being dangerous by the summary.

9. The method of claim 7, wherein altering the treatment for the patient includes aiding in decision-making by a medical professional.

10. The method of claim 1, wherein generalizing the summary includes informativeness ranking based on a comparison of implications of the summary by reviews of a current product or entity to implications by reviews of a different product or entity.

11. A system for document summarization, comprising:

a hardware processor; and a memory that stores a computer program which, when executed by the hardware processor, causes the hardware processor to:

split documents into sentences;

sort the sentences by a metric that promotes review opinion prevalence from the documents to generate a ranked list of sentences, with prevalence being expressed as $$Prev(R, S) = \frac{1}{mn}\sum_{k=1}^{n}\tau_k\rho_k\sum_{i=1}^{m}C(x_i y_k)$$

where R is a set of reviews, Sis a summary, n is a number of sentences, m is a number of reviews, k is an index, i is an index, $\tau_k\rho_k$ is a mask, and C(•,•) is a classifier function for texts x and;

form groups of sentences with similar embeddings and applying a trained generalization encoder-decoder model to output a common generalization of the sentences in each group;

add sentences to a summary from the common generalizations corresponding to the sentences in the ranked list, in rank-order, until a target summary length has been reached; and perform an action responsive to the summary.

12. The system of claim 11, wherein the computer program further causes the hardware processor to simplify the sentences before sorting.

13. The system of claim 11, wherein the computer program further causes the hardware processor to filter trivial conclusions from the sentences before sorting.

14. The system of claim 11, wherein the computer program further causes the hardware processor to sort by a number of implications each sentence has from other sentences.

15. The system of claim 11, wherein the computer program further causes the hardware processor to assign a score to each sentence based on a cosine comparison of encoded sentence representations.

16. The system of claim 15, wherein the score is further discounted by a maximum of previous scores for each sentence.

17. The system of claim 11, wherein the documents are reviews for a healthcare product and wherein the computer program further causes the hardware processor to alter a treatment for a patient based on the summary.

18. The system of claim 17, wherein the computer program further causes the hardware processor to automatically cease a treatment that is indicated as being dangerous by the summary.

19. The system of claim 17, wherein the computer program further causes the hardware processor to aid in decision-making by a medical professional.

20. The system of claim 11, wherein the computer program further causes the hardware processor to rank informativeness based on a comparison of implications of the summary by reviews of a current product or entity to implications by reviews of a different product or entity.

* * * * *